(12) United States Patent
Herlitz

(10) Patent No.: US 9,135,608 B2
(45) Date of Patent: *Sep. 15, 2015

(54) SYSTEMS AND METHODS FOR CONSTRUCTING A LOCAL ELECTRONIC MEDICAL RECORD DATA STORE USING A REMOTE PERSONAL HEALTH RECORD SERVER

(75) Inventor: Sten Herlitz, Boston, MA (US)

(73) Assignee: General Electric Company, Schenectady, NY (US)

( * ) Notice: Subject to any disclaimer, the term of this patent is extended or adjusted under 35 U.S.C. 154(b) by 276 days.

This patent is subject to a terminal disclaimer.

(21) Appl. No.: 13/334,978

(22) Filed: Dec. 22, 2011

(65) Prior Publication Data

US 2012/0095923 A1    Apr. 19, 2012

Related U.S. Application Data

(63) Continuation of application No. 12/421,031, filed on Apr. 9, 2009, now Pat. No. 8,108,311.

(51) Int. Cl.
| | |
|---|---|
| *G06F 21/00* | (2013.01) |
| *G06Q 20/08* | (2012.01) |
| *G06Q 10/00* | (2012.01) |
| *G06Q 20/02* | (2012.01) |
| *G06Q 50/22* | (2012.01) |
| *G06Q 50/24* | (2012.01) |
| *H04L 9/32* | (2006.01) |

(52) U.S. Cl.
CPC ............ *G06Q 20/0855* (2013.01); *G06Q 10/00* (2013.01); *G06Q 20/027* (2013.01); *G06Q 20/085* (2013.01); *G06Q 50/22* (2013.01); *G06Q 50/24* (2013.01); *H04L 9/3247* (2013.01); *H04L 2209/88* (2013.01)

(58) Field of Classification Search
CPC ...................................................... G06F 21/10
USPC .......................................................... 705/51
See application file for complete search history.

(56) References Cited

U.S. PATENT DOCUMENTS

| | | | |
|---|---|---|---|
| 8,108,311 B2 | 1/2012 | Herlitz | |
| 2002/0010679 A1* | 1/2002 | Felsher | 705/51 |
| 2005/0137653 A1* | 6/2005 | Friedman et al. | 607/60 |
| 2010/0262545 A1 | 10/2010 | Herlitz | |

FOREIGN PATENT DOCUMENTS

JP      2008158622 A  *  7/2008

OTHER PUBLICATIONS

Stasia Kahn, Medical Record Privacy and Security in a Digital Environment (IT Professional www.computer.org/itpro vol. 10, No. 2 Mar./Apr. 2008).*

United States Patent and Trademark Office, "Non-Final Rejection," issued in connection with U.S. Appl. No. 12/421,031, mailed on Sep. 23, 2010, 10 pages.

United States Patent and Trademark Office, "Final Rejection," issued in connection with U.S. Appl. No. 12/421,031, mailed on Feb. 22, 2011, 10 pages.

United States Patent and Trademark Office, "Notice of Allowance," issued in connection with U.S. Appl. No. 12/421,031, mailed on Sep. 28, 2011, 14 pages.

* cited by examiner

*Primary Examiner* — James A Reagan

(74) *Attorney, Agent, or Firm* — Hanley, Flight and Zimmerman, LLC

(57) ABSTRACT

Certain embodiments of the present invention provide systems and methods for managing medical information. Certain embodiments provide a local electronic medical record system including a local personal health record (PHR) client, the PHR client downloading encrypted patient documents from a remote PHR server and parsing the downloaded encrypted patient documents to form a local PHR database. The example system also includes an interface receiving user input including an encryption key to decrypt the downloaded encrypted patient documents and displaying patient medical information to the user based on the downloaded decrypted patient documents.

20 Claims, 13 Drawing Sheets

SYSTEMS AND METHODS FOR CONSTRUCTING A LOCAL ELECTRONIC MEDICAL RECORD DATA STORE USING A REMOTE PERSONAL HEALTH RECORD SERVER

RELATED APPLICATIONS

The present application claims the benefit of priority to U.S. patent application Ser. No. 12/421,031, filed on Apr. 9, 2009, entitled "SYSTEMS AND METHODS FOR CONSTRUCTING A LOCAL ELECTRONIC MEDICAL RECORD DATA STORE USING A REMOTE PERSONAL HEALTH RECORD SERVER", which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to systems and methods for managing health care information. Particularly, the present invention relates to systems and methods for generating local electronic medical record systems for secure patient and/or physician access using patient medical record data stored in encrypted form.

In the current medical environment, access to patient medical records is cumbersome and fragmented. Typically, medical records are maintained at individual clinics. If a patient visits more than one clinic, a patient may have a plurality of medical records. For example, a patient may visit a first clinic and create a first medical record and the patient may subsequently visit a second clinic and create a second medical record. If the second clinic does not have access to the first medical record, the examination and diagnosis at the second clinic may be duplicative and inefficient.

The lack of comprehensive medical records is also duplicative and inefficient for the patient. For example, a patient typically fills out similar forms at each clinic the patient attends. The patient may fill out a form with the patient's medical history, various conditions, allergies, heredity information, or other information. The individual clinic then maintains their own record for the patient. As a patient may visit a plurality of clinics throughout their life, the patient may repeatedly fill out the same information. In some circumstances, the patient may not fill out the same information and the various medical records at different clinics may contain partial and/or out-of-date information.

In addition, the decentralized nature of patient medical record information is perpetuated by entities other than medical clinics. For example, medical record information may be maintained by insurance entities, pharmaceutical entities, and/or laboratory entities. An update of the patient medical record at any one of these entities does not ensure the other entities are updated. Accordingly, the patient medical record information differs depending on the entity. Accordingly, it is difficult to locate a medical record that is completely up-to-date and a treating physician may not be able to obtain a complete picture of a patient's health prior to treatment.

Moreover, the decentralized nature of patient medical record information typically does not allow a patient to access their medical records. A patient cannot review a comprehensive report of their medical history and various conditions. The patient generally does not have the ability to access or update their medical records. In addition, the patient does not have the ability to restrict access to their medical records.

As a consequence of patient information being decentralized and a patient not having access to their patient medical record information, the information available to a patient regarding their health status is typically of a general nature. For example, a patient has limited sources of medical information. One of the sources a patient may attempt to gather information from is the Internet. A patient may search for medical information on the Internet and find various web sites providing general information about the condition. Some of the information may be applicable to the context of the patient and some of the information may not. A patient may have difficulty in sorting through the available information and determining what information is applicable to their circumstances.

Centralized systems, such as Google Health and Microsoft HealthVault, attempt to address some of these issues, however due to limited connectivity to medical providers and other data sources, they too are unable to present a full picture of a patient's medical information. Moreover, the largest roadblock to full adoption of these systems may be the severity of the privacy concerns with respect to the handling and storing of protected health information (PHI) by non-medical, third-party companies.

Where information is gathered, Electronic Medical Record (EMR) systems typically run on local servers and use a local patient database, but this can be expensive in terms of hardware, software, maintenance, backup, etc. For simplicity, some systems are instead hosted remotely and accessed via the Web. While this approach can lower cost, it also opens up a data security risk. Sensitive data stored remotely is potentially subject to hackers and rogue administrators, for example.

SUMMARY OF CERTAIN EMBODIMENTS OF THE INVENTION

Certain examples provide systems and methods for managing medical information.

Certain embodiments provide a local electronic medical record system including a local personal health record (PHR) client, the PHR client downloading encrypted patient documents from a remote PHR server and parsing the downloaded encrypted patient documents to form a local PHR database. The example system also includes an interface receiving user input including an encryption key to decrypt the downloaded encrypted patient documents and displaying patient medical information to the user based on the downloaded decrypted patient documents.

Certain embodiments provide a computer-implemented method for providing a local electronic medical record system. The method includes downloading encrypted patient documents from a remote personal health record (PHR) server to a local PHR client. The method also includes parsing the downloaded encrypted patient documents to form a local PHR database. The method further includes decrypting the downloaded encrypted patient documents using an encryption key. Additionally, the method includes displaying patient medical information to a user based on the downloaded decrypted patient documents.

Certain embodiments provide a computer-readable medium including a set of instructions which, when executed on a computer, implement a local electronic medical record system. The set of instructions includes a local personal health record (PHR) client, the PHR client downloading encrypted patient documents from a remote PHR server and parsing the downloaded encrypted patient documents to form a local PHR database. The set of instructions also includes an interface receiving user input including an encryption key to decrypt the downloaded encrypted patient documents and displaying patient medical information to the user based on the downloaded decrypted patient documents.

Figure 1:
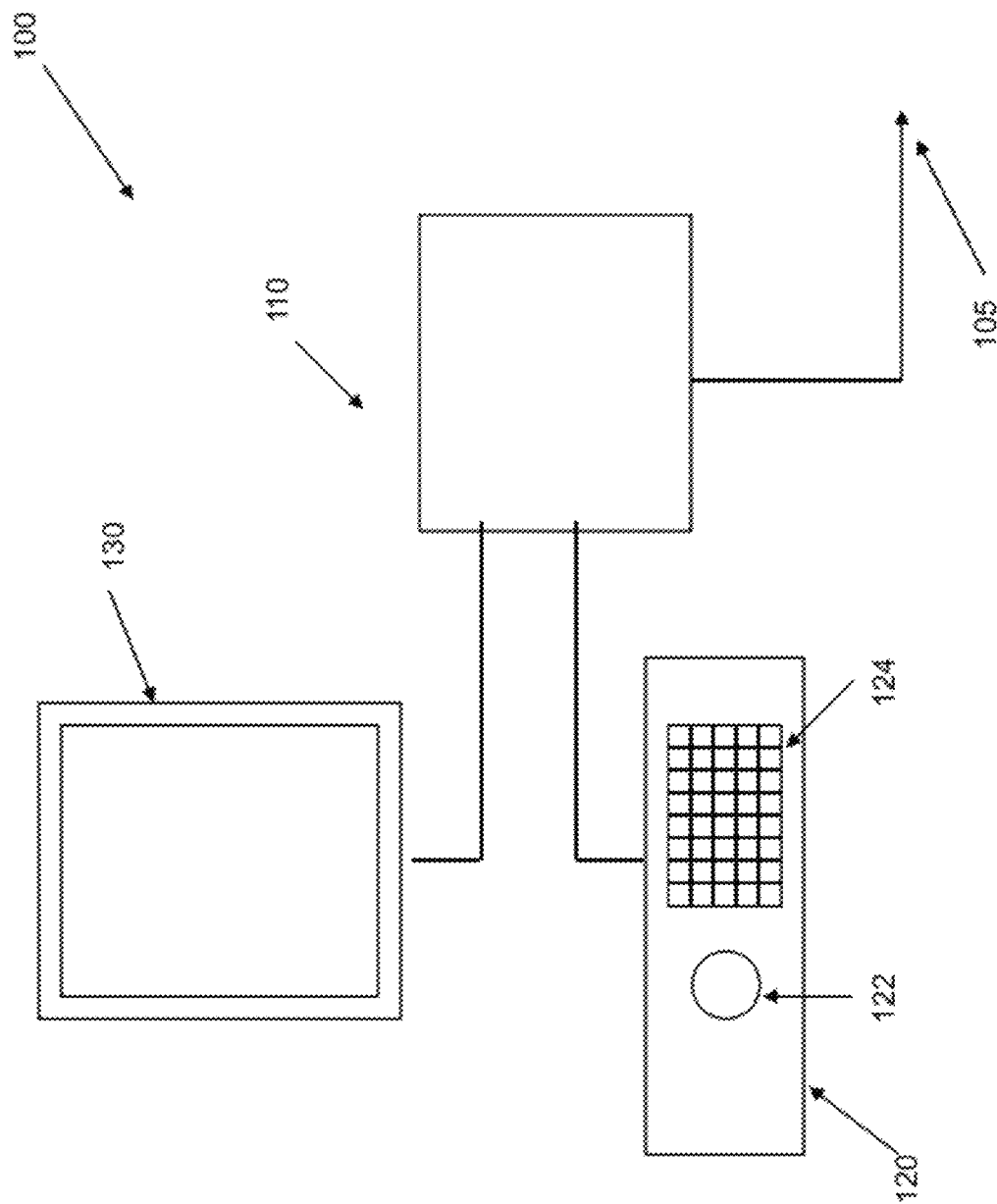
FIG. 1 illustrates an example system for acquiring and communicating information.

The foregoing summary, as well as the following detailed description of certain embodiments and/or examples, will be better understood when read in conjunction with the appended drawings. For the purpose of illustrating the presently disclosed technology, certain embodiments and/or examples are shown in the drawings. It should be understood, however, that the presently described technology is not limited to the arrangements and instrumentality shown in the attached drawings.

DETAILED DESCRIPTION OF THE INVENTION

Although the following discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

The example methods and systems described herein construct a local data store (e.g., a multi-patient database for physicians) on a user's computer by parsing downloaded Personal Health Record (PHR) documents. The downloaded PHR documents can also be stored locally as separate files, for example. The local data store provides off-line access to patient information as well as a performance advantage gained by using local data rather than remote data. The local data store/data file(s) act as a cache for physician and/or other authorized user access. For example, if a record is deleted, it can be rebuilt from downloaded PHR information. In certain examples, local storage of information is reduced or eliminated. Local storage can be implemented in a variety of ways, including but not limited to one or more files, databases, and/or combination(s) of file(s) and database(s), for example.

PHR systems can include various clinical documents (such as a Clinical Document Architecture (CDA) care encounter document, Continuity of Care Record (CCR) data summary document, etc.) that can be displayed directly to the user. Traditional PHR servers often decompose these documents into distinct data elements and store the data elements in a database and/or other data store so that the data can be retrieved in a different format than the original documents. This, however, opens up a data security risk—if the PHR server can access the data in unencrypted form, so can rogue administrators and hackers.

A remote PHR server is used for data storage and retrieval. The PHR server and its data store process exclusively encrypted data to help guarantee patient privacy, for example. The PHR server cannot be used to decrypt the encrypted data. Only client-side software interacts with medical data structures, allowing the PHR server to streamline its operations and become more efficient. Client-side software (e.g., clinic-side software) encrypts the data before uploading the data to the PHR server. Software, such as clinic- or patient-side software, decrypts the data after downloading it to a local computer for authorized access. Client-side encryption helps to guarantee privacy as opposed to current PHR systems where patients just have to "trust" that their data will not be misused. For physician offices, for example, an additional advantage over a traditional electronic medical record (EMR) system is that it involves no local servers (and therefore no maintenance, backup, or security concerns).

Not only does the approach outlined above reduce the cost of an EMR system, it also eliminates the need to duplicate data across EMR and PHR systems, as the two systems are effectively one system in this architecture. A medical record can be owned by a patient as it is stored in the PHR data store using a patient-specific encryption key, and the patient can control access to the data. Rather than saving new data locally, a physician EMR system uploads the new data to the PHR, as would other PHR data providers such as other clinics, hospitals, labs, pharmacies, health information exchanges (HIE's), etc.

In certain examples, records of active patients can be cached in a local database at a clinic. However, EMR software would check with the PHR server for content update(s) before using locally cached data.

Conventional Web-based EMR systems expose data to risks associated with storing sensitive data on a remote third-party server, and offer no tie-ins to PHR systems for patient access. By using a secure PHR server as the backend for a Web-based physician EMR application, the security problem of storing sensitive data remotely is avoided by the PHR system architecture (where the server never sees any unencrypted data), and PHR access is provided for the patient.

Rather than trying to convert paper-based medical records for all patients in a clinic at one time, conversion to electronic records can be performed incrementally. For example, as a patient comes in, a PHR patient identifier (ID) can be generated, and the office staff can scan/convert the corresponding paper-based medical record and upload it to the PHR.

In certain examples, PHR/EMR access can be facilitated using physician-side software in a PHR system. Physician access to a patient's online PHR can substitute for the presence of a traditional EMR system, as well as facilitate physician access to patient information during emergencies and/or other cases when a patient is new to a hospital or clinic, for example.

In certain examples, software running on a patient's computer can download encrypted clinical documents from a PHR server and decrypt the documents locally. The patient computer can then decompose the decrypted clinical documents into a small, single-patient database. The software can then display the medical record in many different ways (including in original document form, for example). The database file can be stored locally on the patient's computer for quicker future access. Technologies such as Java applets, Adobe® Flash/Flex, and/or Microsoft Silverlight™ can be used for data storage and retrieval.

Thus, certain examples can display medical record data to a patient in a variety of ways in addition to static clinical documents representing snapshots in time of a specific data subset. Having the data in a structured database format, for example, makes it possible to present the medical record data in many different ways. Representing the data in a single-patient database on the patient's home computer improves flexibility and performance, and also allows it to be available off-line. Display of medical record data can be facilitated without compromising security on the PHR server.

FIG. 1 illustrates an example system 100 for acquiring and communicating information. The system 100 includes a computer unit 110. The computer unit 110 can be any equipment or software that processes electronic data. For example, the computer unit 110 can be a personal computer. The computer unit 110 can have at least one processor and memory. The computer unit can receive input from a user. The computer unit 110 can be connected to other devices as part of an electronic network. In FIG. 1, the connection to the network is represented by line 105. The computer unit 110 can be connected to network 105 physically, by a wire, or through a wireless medium.

The system 100 also includes an input unit 120. The input unit 120 can be a console having a track ball 122 and keyboard 124. Other input devices can be used to receive input from a user as part of the input unit 120. For example a microphone can be used to receive verbal input from a user. The system 100 also includes at least one display unit 130. The display unit 130 can be a typical computer display unit. The display unit 130 can be in electrical communication with the computer unit 110 and input unit 120. In an example, the display unit 130 can represent multiple display units or display regions of a screen. Accordingly, any number of display units can be utilized in accordance with the present invention. The computer unit 110 and display unit 130 can be separate units or be part of a single unit. In the case of separate units, the display unit 130 can be in electrical communication with the computer unit 110. The components of the system 100 can be single units, separate units, can be integrated in various forms, and can be implemented in hardware and/or in software. The system 100, or some variation thereof, can be used by a patient to access patient medical information and the system 100 can also be used by a clinic to access patient medical information.

Figure 2:
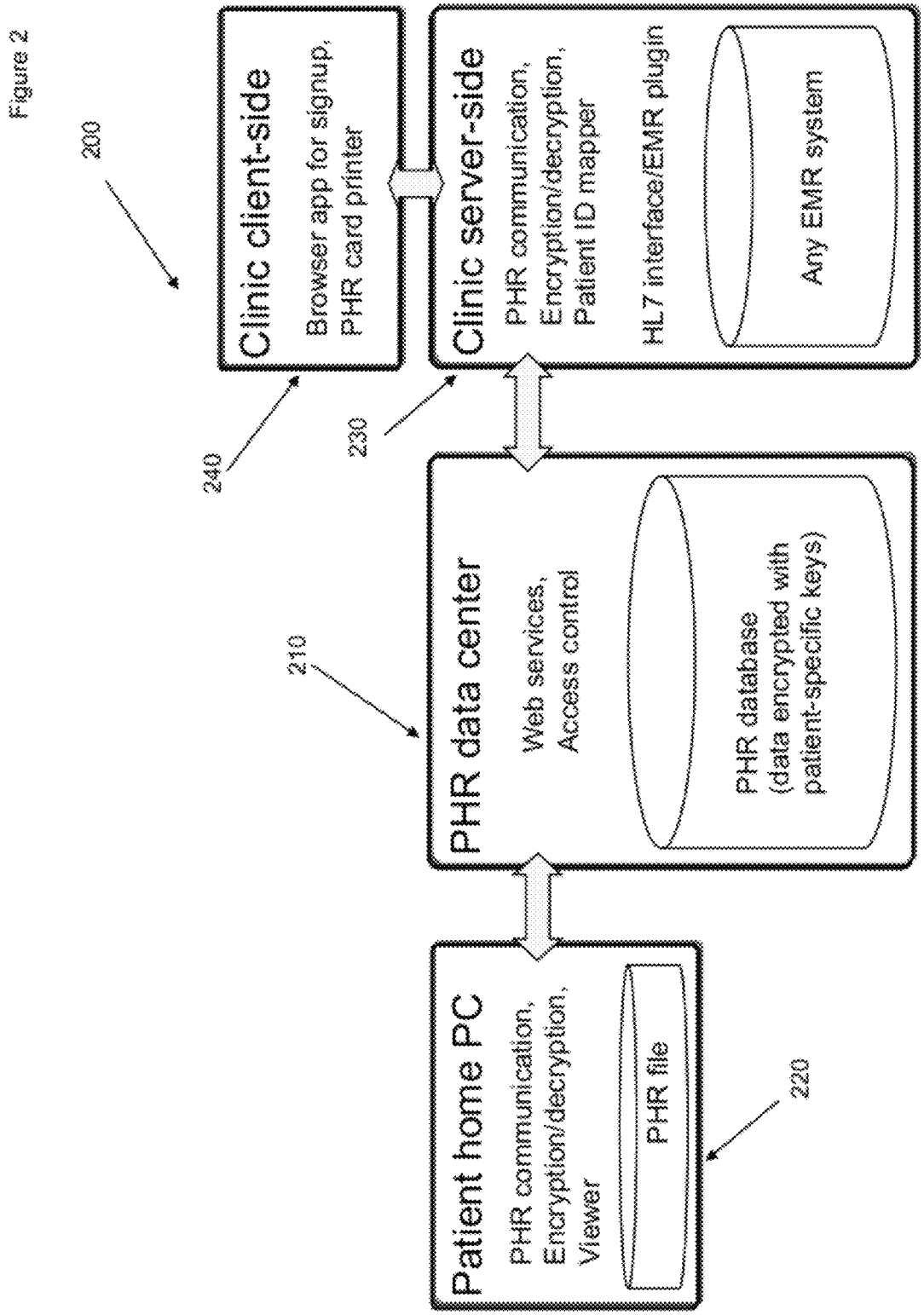
FIG. 2 illustrates a system for managing medical information.

FIG. 2 illustrates an example system 200 for managing medical information. The system 200 includes a data center 210, a patient interface 220, a clinical server 230, and a clinical client 240. In an example, the data center 210 is a database and/or other data store for storing patient medical record data and associated audit logs in encrypted form, accessible to the patient as well as authorized medical clinics (including hospitals, doctor's offices, and/or other diagnosis/treatment facilities). In an example, the data center 210 can be a server or a group of servers and/or reside on a server or group of servers, for example. The data center 210 can also be one server or group of servers that is connected to other servers or groups of servers at separate physical locations. The data center 210 can represent single units, separate units, or groups of units in separate forms and can be implemented in hardware and/or in software. In an example, the data center 210 receives medical information from a plurality of sources. For example, the sources of medical information can include various clinics, labs, pharmacies, as well as the patient him/herself.

In an example, the data center 210 can represent a central database for storing encrypted update-transactions for patient medical records, including usage history. In an example, the data center 210 also stores the patient medical records. The data center 210 stores and controls access to encrypted information. In an example, medical records can be stored without using logic structures specific to medical records. In such a manner the data center 210 is not searchable. For example, a patient's data can be encrypted with a unique patient-owned key at the source of the data. The data is then uploaded to the data center 210. The data center 210 does not process or store unencrypted data thus minimizing privacy concerns. The patient's data can be downloaded to, for example, a computer unit and decrypted locally with the encryption key. In an example, accessing software, for example software used by the patient and software used by the medical clinic performs the encryption/decryption.

Figure 8:
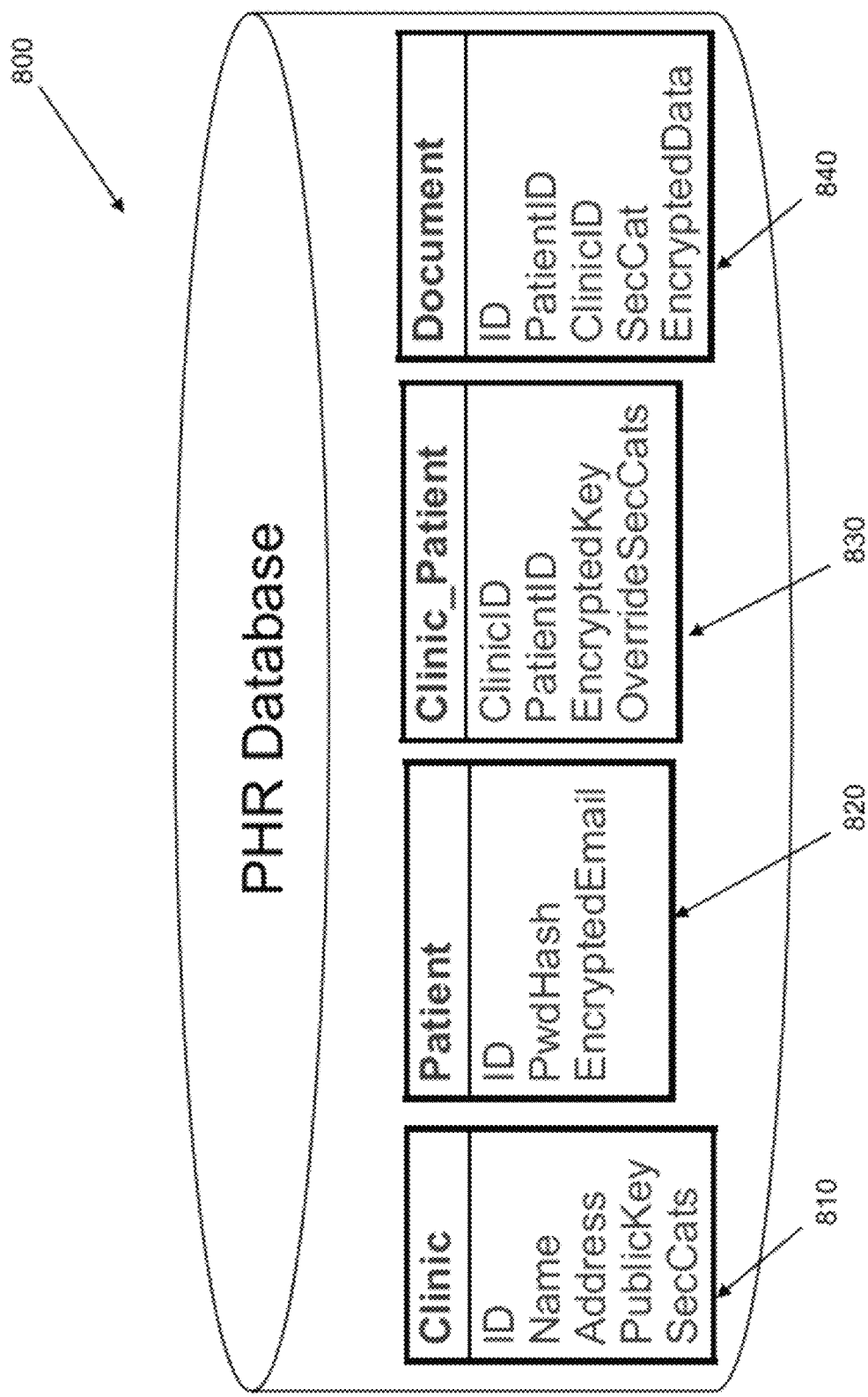
FIG. 8 illustrates an example personal health record (PHR) database used with a data center as described herein.

As illustrated, for example, in FIG. 8, the data center 210 can include a personal health record (PHR) database 800. As shown, for example, in FIG. 8, the database 800 can be structured according to clinic, patient, patient/clinic association, and document. Clinic information 810 can include, for example, an identifier, a name, and address, a public key, and one or more security categories. Patient information 820 can include, for example, an identifier, a password hash, and an encrypted email address. Patient/clinic association information 830 can include a clinic identifier, a patient identifier, an encrypted key, and one or more override security categories. Document information 840 can include an identifier, a patient identifier, a clinic identifier, a security category, and encrypted data, for example.

The data center 210 can maintain a registration of patients and a registration of medical clinics. Medical clinics can be registered in the data center 210 with name, address, and other identifying information. The medical clinics are issued an electronic key that is associated with a certificate. The medical clinics are also granted a security category. The security category is typically based on clinic type. In an example, the requests and data sent from medical clinics are digitally signed with the clinic's certificate and authenticated by the data center 210. Patients can be registered in the data center 210 with a patient identifier and password hash, without any identifying information. Typically, registered patients are issued a token containing a unique patient identifier and encryption key. The token can be, for example, a paper card, a magnetic card, a fob card, or some other equipment that can be used to identify the patient. A patient can access the data center 210 utilizing their token, and in an example, a user identifier and password.

The data center 210 is in communication with the patient interface 220 and the clinical server 230. The data center 210, patient interface 220, and clinical server 230 can be in communication via any computer hardware and/or software that can process electronic communications to/from the data center 210, patient interface 220, and/or clinical server 230. For example, communication can include the computer unit 110, as shown in FIG. 1. In an example, communication can occur using a card reader unit. The card reader unit can be a magnetic card reader that can process data when a magnetic card is passed through a receptacle, for example. In addition the card reader unit can receive communication from other types of devices, such as for example a fob card, universal serial bus flash memory, or other type of memory equipment and/or software.

The user can download a medical record from the data center 210, decrypt the medical record on the patient interface 220, such as a personal or handheld computer, and then process the data on a local basis, for example.

Similarly, a clinical client interface 240 can be used to download medical record information from the clinical server 230 and/or data center 210. For example, medical record information can be stored on the clinical server 230, such as in an electronic medical record (EMR) system and be accessible by the clinical client 240 from the server 230. As another example, medical record information can be stored at the data center 210 and can be accessible by the clinical client 240 via the clinical server 230, which requests the information from the data center 210.

In certain examples, one or more of the patient interface 220, clinical server 230, and/or clinical client 240 can be used to send data to the data center 210 for medical record update. Alternatively and/or in addition, sources such as laboratory results, pharmaceutical information, patient examination information, and image acquisitions, can provide data for storage at the data center 210. In certain examples, a patient can register or log in association with a patient identifier. Data can then be encrypted using the patient identifier and patient encryption key and sent to the data center 210 to update the patient's medical record. Also, the data can be normalized prior to sending to the data center 210.

In an example, data center 210, patient interface 220, clinical server 230, and/or clinical client 240 can be connected to one or more of each other via network connections, for example through the Internet or private network.

Figure 3:
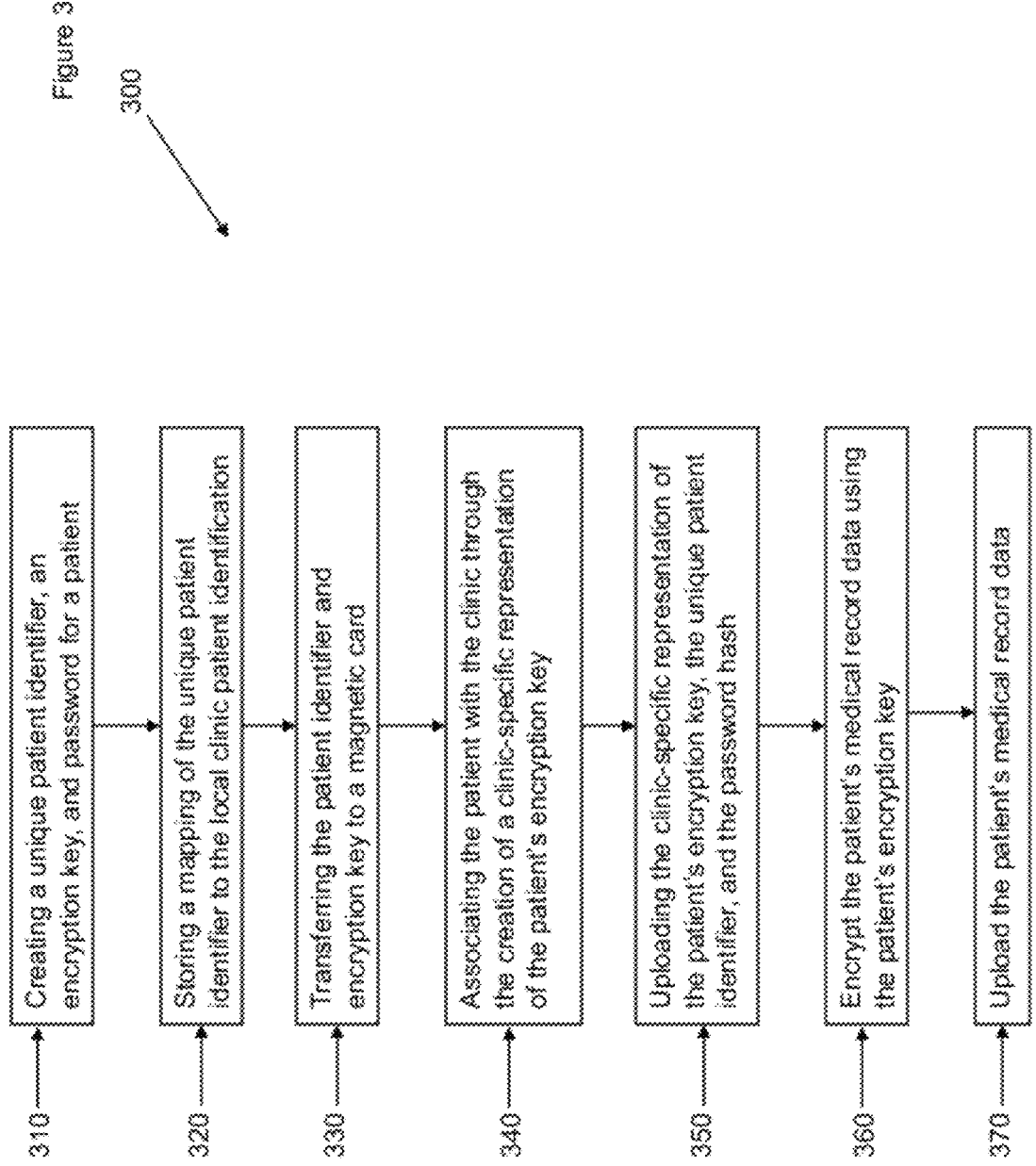
FIG. 3 illustrates an example method for managing medical information.

FIG. 3 illustrates an example method 300 for managing medical information. The method 300 illustrates a method that is performed upon an initial encounter with the patient and typically the patient does not yet possess a medical card. In an example a patient visits a clinic, for example to receive medical treatment. At 310, computer software typically executing on a computer at the clinic generates a unique patient identifier, a unique encryption key, and password for the patient. In an example, the unique encryption key is a symmetric encryption key in that the same encryption key is used for encryption and decryption. At 320, the unique patient identifier is mapped with the patient identifier used by the local clinic. The mapping is locally stored by the clinic. At 330, the patient identifier and encryption key are transferred onto a medical paper card or magnetic card. Alternatively, the patient can be issued a fob card or other type of device. The medical card allows the patient to control and access their own medical record. At 340, the patient is associated with the clinic through the creation of a clinic-specific representation of the patient's encryption key. In an example, the patient is associated with the clinic through the creation of the clinic-specific representation by encrypting the patient's encryption key with the clinic's public key. In an example, the clinic's public key is part of a public/private key pair used for asymmetric encryption. A first key can be used to encrypt and a second key can be used to decrypt. For example, the first key can be a public key that is used if one wants to ensure only the owner of the private key has access. The owner of the private key can encrypt with the private key to allow others to authenticate that a message originated from the owner. The clinic-specific representation of the patient's encryption key can then be stored in a database. The clinic-specific representation allows the clinic the ability to access the patient's medical records without storing the patient's encryption key locally or possessing the patient's medical card. At 350, the clinic-specific representation of the patient's encryption key, the patient identifier, and the password hash are uploaded to a database or other server/storage type unit. In an example, the database stores the clinic-specific representation of the patient's encryption key, the unique patient identifier, the password hash, and the associated clinic information. At 360, the patient's medical record data is encrypted using the patient's encryption key. In an example, the medical record data is encrypted by computer software operating on equipment at the clinic. At 370, the encrypted medical record data is uploaded to a database or other server/storage type unit. The encrypted medical record data is stored at the database. In an example, the medical record data can be optionally tagged with a security category. The tagging of the medical record data with a security category provides a layer of security in that a clinic without the appropriate security privileges cannot download the tagged medical record data. In an example, a clinic that is associated with the patient cannot download the tagged medical record data if the clinic does not have the appropriate security privileges.

Figure 4:
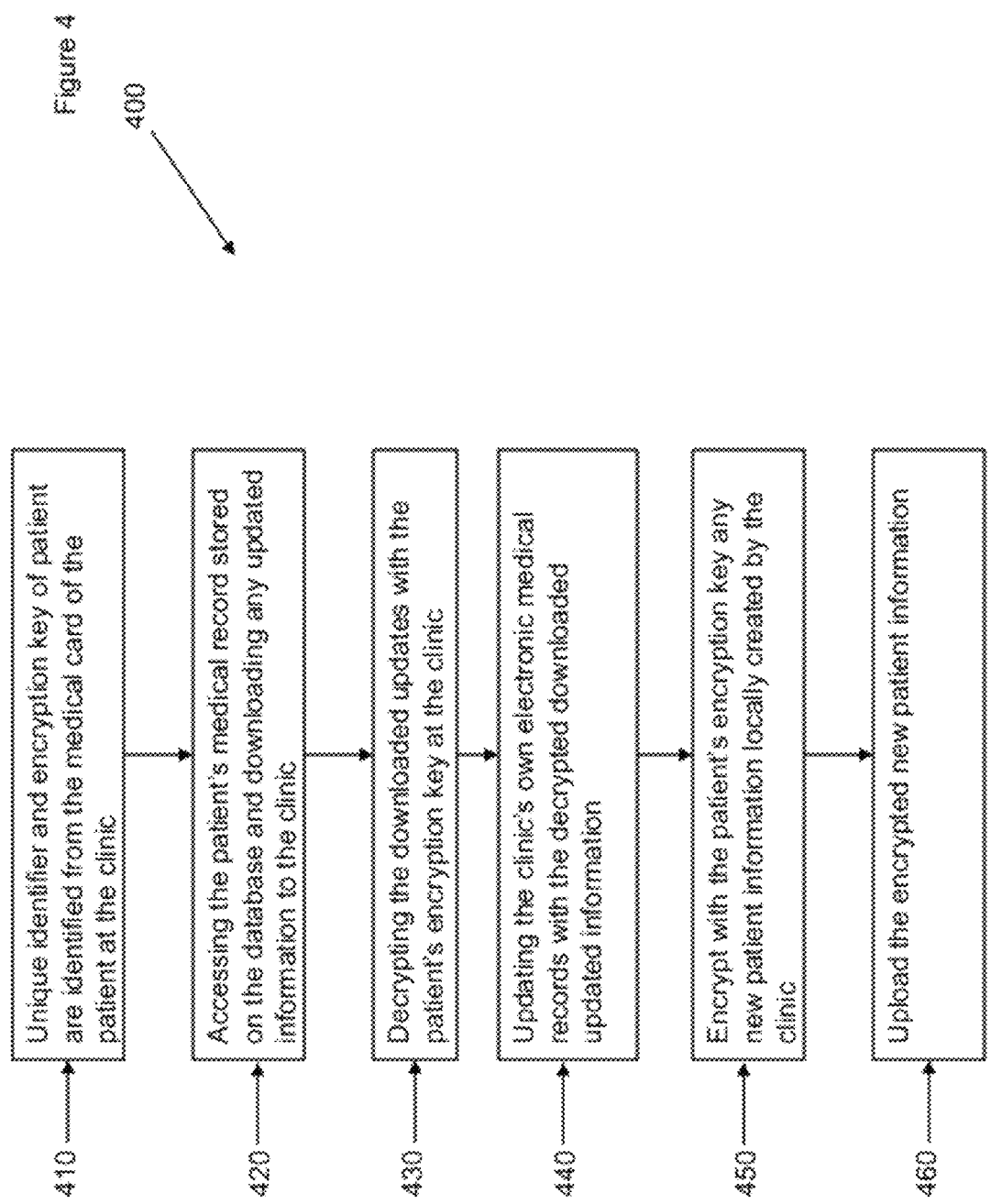
FIG. 4 illustrates an example method for managing medical information.

FIG. 4 illustrates an example method 400 for managing medical information. The method 400 illustrates a method that is performed upon a typical encounter with the patient after the patient has been issued a medical card. At 410, the unique identifier and encryption key of a patient are identified from the medical card of the patient at the clinic. In an example, the patient can swipe their medical card at the reception area of the clinic. The medical card can be processed by computer software at the clinic. Optionally, a tablet device can be used at the front desk to capture patient consent for various security clearances or confirmations. Alternatively, the unique identifier and encryption key of a patient are located by the clinic. In an example where the clinic does not have a card reader or when the patient does not have access to his card, the clinic can look-up the unique patient identifier using the mapping stored locally. The clinic can obtain the patient encryption key by downloading the encrypted version of the key from the database and decrypting it using the private key of the clinic.

At 420, the clinic can access the patient's medical record stored on the database. The clinic can send a download request containing the unique patient identifier. In an example, the download request is digitally signed with the clinic's private key allowing the database to check the signature using the registered public key of the clinic. The database can also check the registered security categories of the clinic and disallow downloads for any patient record transactions for which the clinic does not have adequate security privileges. The clinic can then download any updated medical record information in encrypted form. At 430, the downloaded updates are decrypted with the patient's encryption key. In an example, the downloaded updates are decrypted by computer software executing on a computer at the clinic. At 440, the new downloaded information that has been decrypted is used to update the clinic's own electronic medical records. At 450, any new patient information that has been created locally by the clinic is encrypted with the patient's encryption key. At 460, the encrypted data is uploaded to the database. In an example, the computer at the clinic can be set to upload new information on a regulated schedule, such as on a nightly basis. In an example, the new information can be optionally tagged with a security category. The tagging of the new information with a security category provides a layer of security in that a clinic without the appropriate security privileges cannot download the tagged new information. In an example, a clinic that is associated with the patient cannot download the tagged new information if the clinic does not have the appropriate security privileges. In an example, a clinic server sends an email and/or other electronic communication alerting a patient that new information is available (e.g., lab results).

In an example, a patient can be referred from a first clinic to a second clinic. The second clinic can desire to view the patient's medical record before the patient checks-in to the second clinic. In such a scenario, the first clinic can download the public key of the second clinic and use the public key of the second clinic to encrypt the patient's encryption key. The first clinic can upload the encrypted key of the patient, creating an association between the patient and the second clinic. Once the second clinic has retrieved the patient's key, the second clinic can download the patient's medical record prior to the patient's arrival.

In an example, the scenario of a patient being separated from his medical card is contemplated. For example, a patient can lose his medical card. The medical card is typically not usable if found by another person because the finder of the medical card does not have the password. In the example of the lost medical card, the patient can report the lost card to the clinic. The clinic can download the encrypted key of the patient and decrypt the patient's key with the clinic's private key. The clinic can issue a new medical card to the patient. For increased security, the clinic can also change the encryption key of the patient. In order to change the encryption key of the patient, the clinic can download the available transactions for the patient. The clinic can generate a new encryption key for the patient. The clinic can decrypt the available transactions with the old patient key and re-encrypt the available transactions with the new patient key. The clinic can then upload the available transactions to a database. The clinic can then download the public keys for the clinics associated with the patient. For the associated clinics, the new patient key is encrypted with the respective clinic's public key. The clinic can then upload the new clinic-specific encrypted patient keys.

Figure 5:
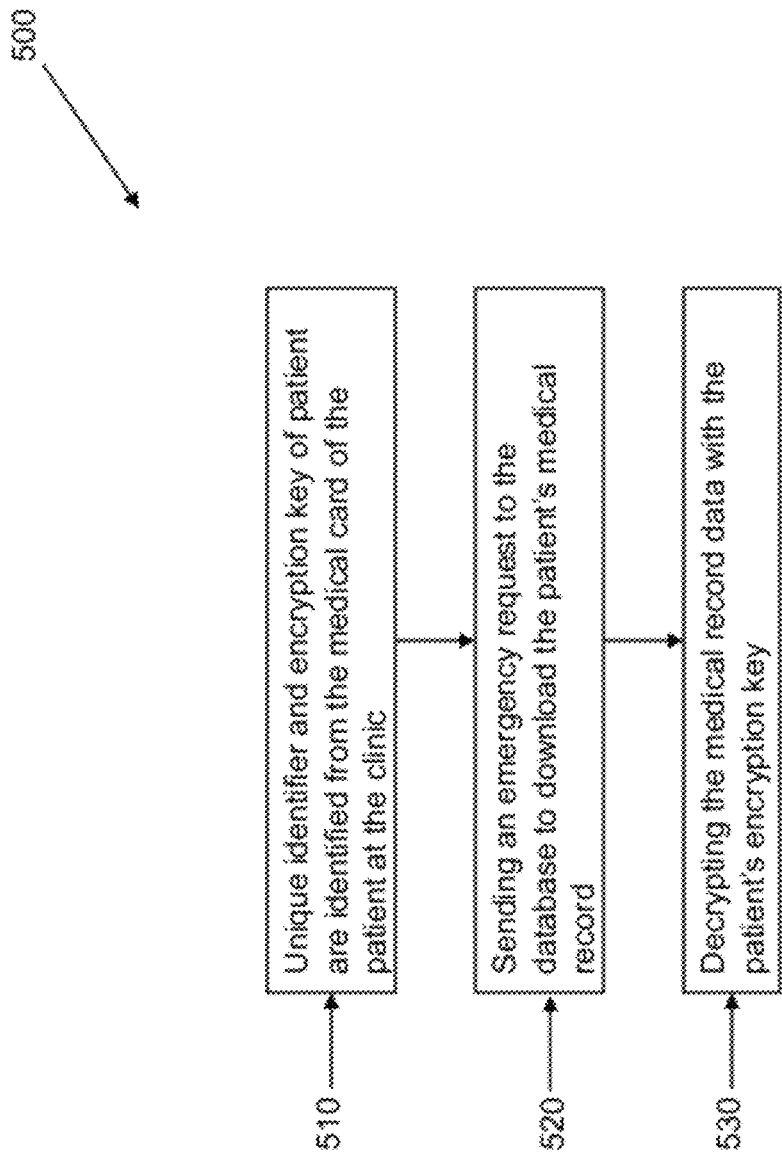
FIG. 5 illustrates an example method for managing medical information.

FIG. 5 illustrates an example method 500 for managing medical information. The method 500 illustrates a method that is performed upon an emergency encounter with the patient, for example an unconscious patient is brought into an emergency clinic and the emergency clinic is not associated with the patient. If the patient is carrying his or her medical card, the method 500 can be performed. At 510, the unique identifier and encryption key of the patient are identified from the medical card of the patient. In an example, an emergency medical technician or other health care professional can "swipe" the medical card of the patient. Computer software can receive the information from a card reader. In an example, an emergency medical technician can have a wireless tablet computer with the ability to read magnetic cards. The emergency medical technician can access the medical records of the patient prior to arriving at the emergency clinic. At 520, after the medical card has been "swiped" the health care professional can send an emergency request to the database using computer software to download the patient's medical record. The emergency request can be a code provided to emergency care providers that enables the emergency care providers to access a patient's medical records if the emergency care provider has the patient's encryption key and unique identifier. At 530, computer software at the emergency clinic decrypts the medical record data with the patient's encryption key. The emergency clinic then has access to the patient's medical records and can make a more efficient and accurate diagnosis.

Figure 6:
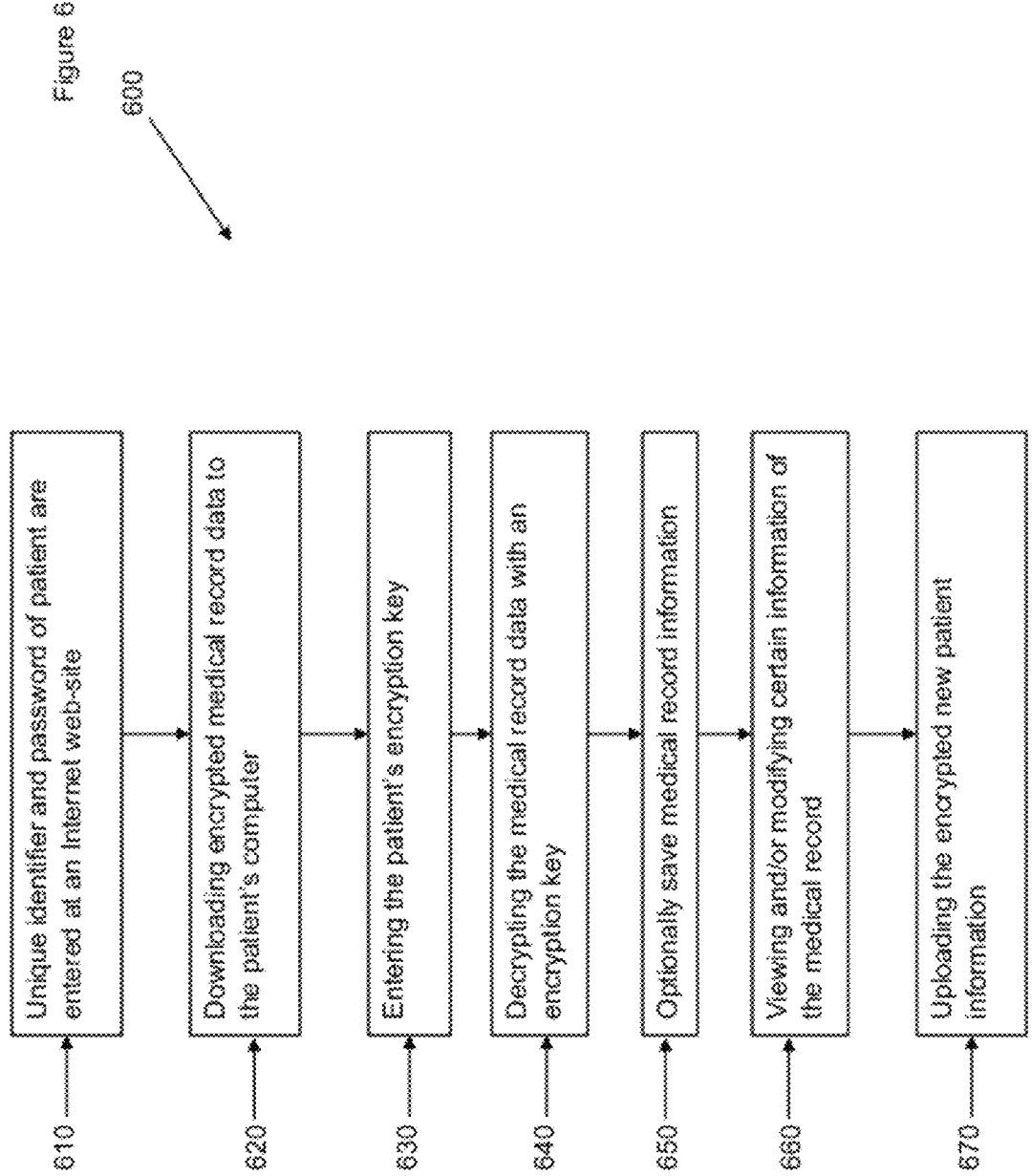
FIG. 6 illustrates an example method for managing medical information.

FIG. 6 illustrates an example method 600 for managing medical information. The method 600 illustrates a method that is performed when the patient requests access to their medical records through a computer. For example, the patient can desire to access their medical records using a personal computer at home. At 610, in an example the patient enters the patient identifier and password at an Internet website. At 620, the encrypted medical record data is downloaded to the patient's computer. At 630, the patient's encryption key is entered. In an example, the patient can store the encryption key on a local disk for convenience. Alternatively, the patient's computer can have a magnetic card reader. The patient can enter the encryption key using the magnetic card reader or other device. At 640, the medical record data is decrypted using the encryption key. At 650, the patient can optionally save the medical record information on a local disk for offline access. At 660, the patient can view and/or modify certain information of the medical record. For example, the patient can view their medical records and history. In an example, the patient does not have the ability to modify the entries from clinics or other sources. The patient can add comments or modify security clearances. For example, the patient can add comments regarding the side effects of certain medications. The patient can also modify the access rights of certain clinics. For example, the patient can revoke a clinic's access rights by disassociating the patient from the clinic. The patient can modify a clinic's access rights by overriding the default security categories. The patient can request a clinic or other source upload any new information. The patient can acknowledge the receipt of laboratory results or other clinical information. At 670, the patient can upload any modified information using the assigned encryption key.

Figure 7:
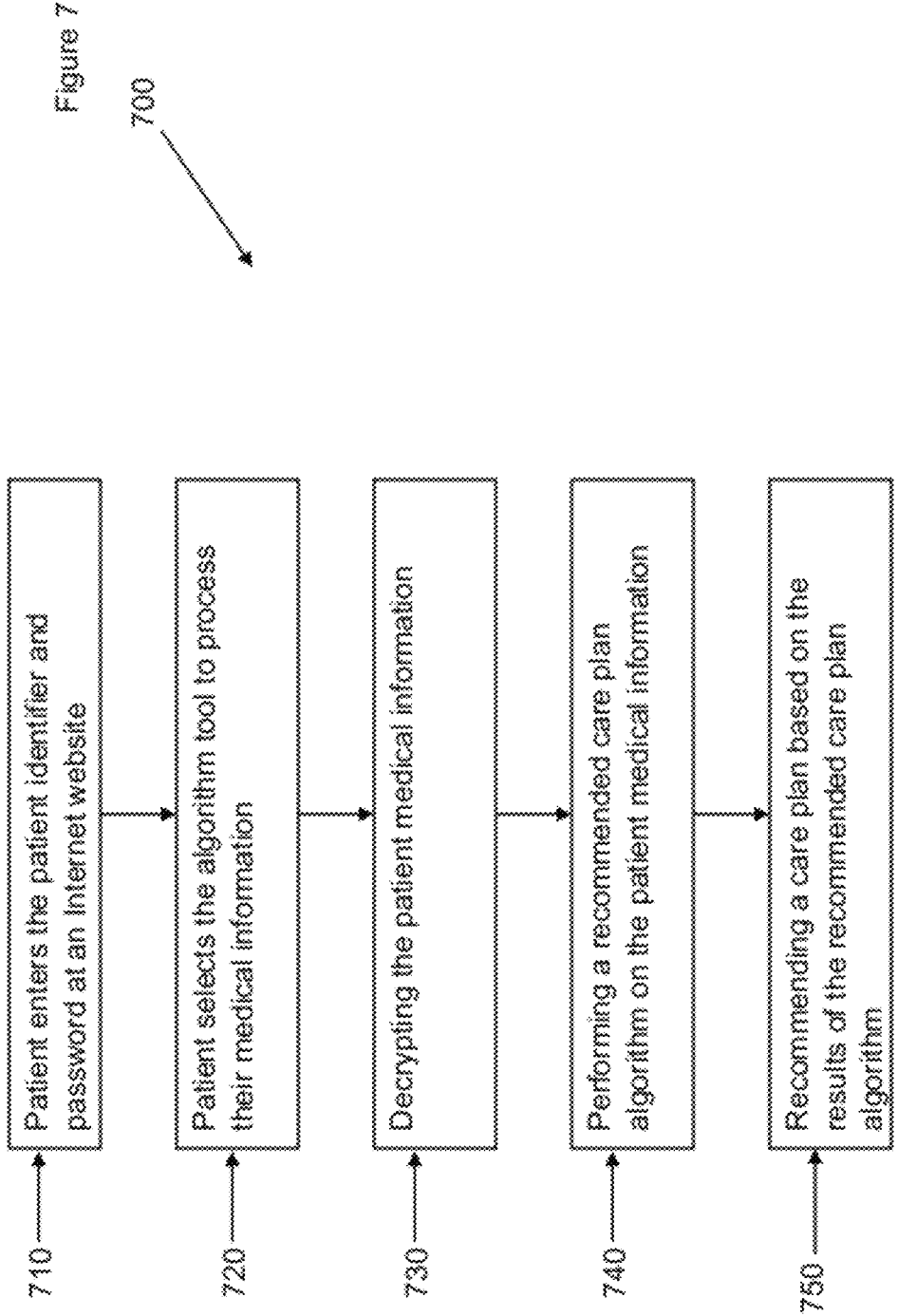
FIG. 7 illustrates an example method for managing medical information.

FIG. 7 illustrates an example method 700 for managing medical information. The method 700 illustrates a method that is performed when the patient logs into a website to access medical information. The website can present the patient with the option of receiving health information in context of the patient's medical information. For example, computer software/instructions can execute to process the medical information available in the encrypted documents downloaded from data center 210 for a medical patient and return information about the conditions of the patient to the patient.

For example, at 710, in an example the patient enters the patient identifier and password at an Internet website. The patient identifier and password grant the patient access to a set of tools. Tools and/or other functionality available to a patient via a website and/or via the patient's computer (e.g., the patient interface 220) include matching technology/tools, education/information, guided feedback, etc. At 720, a patient can select a tool to process their medical information.

At 730, the patient data is decrypted. Accordingly the patient can download the medical record from the database 210, decrypt the medical record on the patient's computer and execute the computer software on the patient's computer.

At 740, a processor executes program code according to a selected tool and/or other functionality. For example, the processor can execute program code to perform a recommended care plan algorithm. The recommend care plan algorithm receives data from the patient's medical record and processes the data. Based on the data available, the recommended care plan algorithm outputs a recommended care plan for the patient. The recommended care plan algorithm can identify, among other things, the patient's conditions and degree of severity of the conditions. The recommended care algorithm can also consider data such as sex, age, height, weight, heredity, lifestyle factors, activity level, and/or other factors. The recommended care plan algorithm can utilize these factors and provide a recommended care plan. The recommended care plan can include techniques for improved health based on the patient's condition. For example, the recommended care plan can include diet recommendations to an individual that has been diagnosed with diabetes.

At 750, in an example, a memory includes program code executable by the processor for providing a recommendation or other output based on selected tool or other functionality. For example, program code executes to recommend a care plan based on the results of the recommended care plan algorithm. The recommended care plan can include techniques for improved health based on the patient's condition. For example, the recommended care plan can include diet recommendations to an individual that has been diagnosed with diabetes. The recommended care plan is typically customized to the patient and provides recommendations and information based on the specific health of the patient as opposed to generalized information.

As an alternative example, at 740, the memory includes program code executable by a processor for performing a sponsored information algorithm. In such an example, 710 is executed as described above. In an example, 720 is not executed as the sponsored information handling can be automatic. The patient cannot select an algorithm tool. Block 730 is executed as described above. At 740, the sponsored information algorithm receives data from the patient's medical record and processes the data. Based on the data available, the sponsored information algorithm outputs sponsored information for the patient. At 750, the memory includes program code executable by the processor for providing sponsored information based on the results of the sponsored information algorithm. The sponsored information can include educational material, product/service offerings, or other advertisements, for example.

In operation and for example, a patient that has recently been diagnosed with diabetes can receive information from the treating physician. The physician can log the diagnosis and treatment specifics in the patient's electronic medical record. In addition, various tests and laboratory information can be recorded as part of the patient's electronic medical record, or can be recorded separately. Similarly, the pharmaceutical information can be recorded as part of the patent's electronic medical record or can be recorded separately. In an example, the medical information is sent in encrypted form to the data center 210. In an example, the medical information is normalized by the sources of the information prior to sending to the data center.

Figure 9:
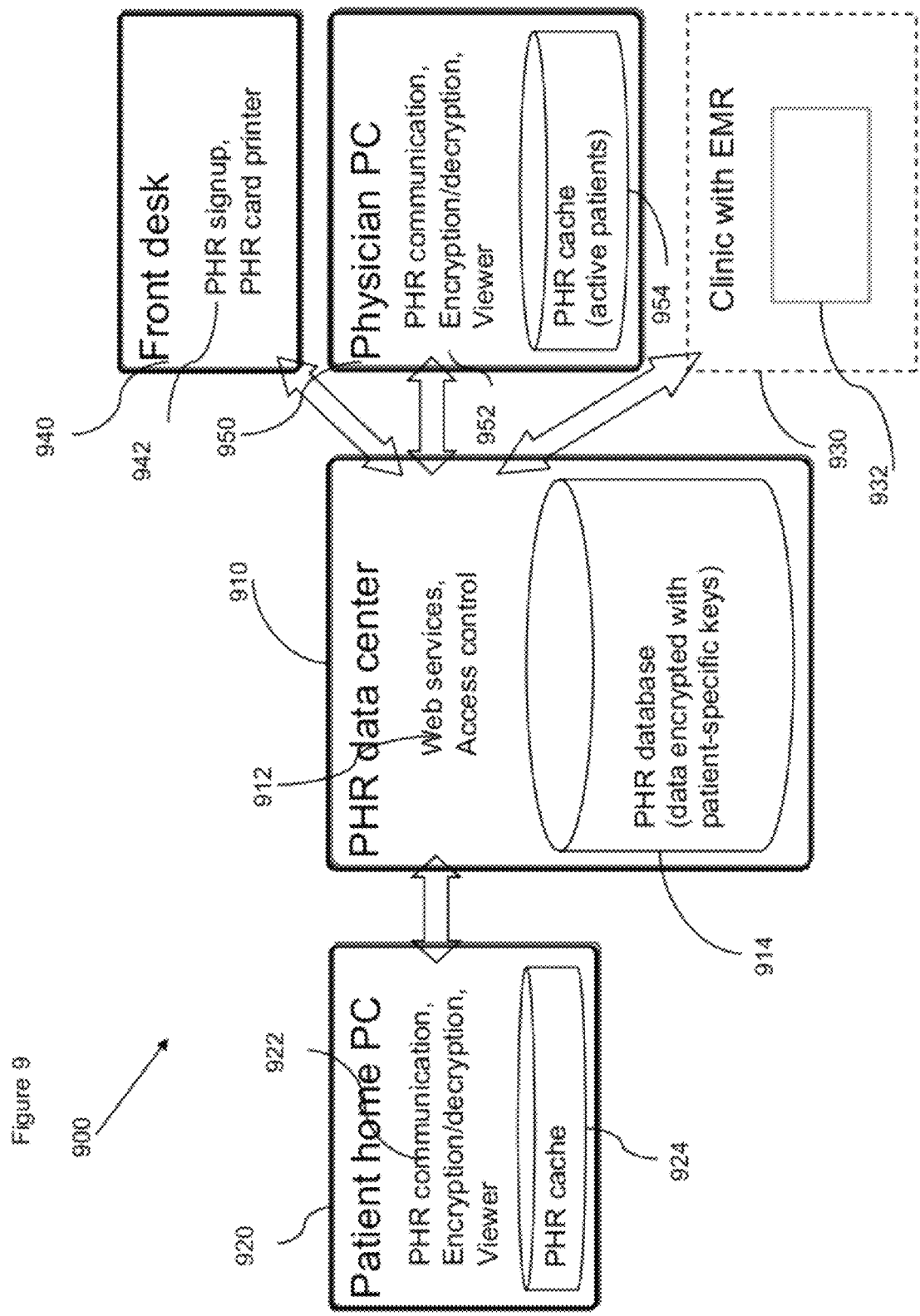
FIG. 9 illustrates an example PHR system for managing clinical information at a physician office.

In addition to clinic PHR/EMR systems and methods, information and access can be provided via a local user computer with access to a remote server (e.g., a remote PHR server). FIG. 9 illustrates an example PHR system 900 for managing clinical information at a physician office. The system 900 includes a data center 910, a patient home computer 920, a clinic server 930, a front desk or reception interface 940, and a physician computer 950.

In an example, the data center 910 includes a PHR database and/or other data store 914 for storing patient medical record data and associated audit logs in encrypted form, accessible to the patient as well as authorized medical clinics (including hospitals, doctor's offices, and/or other diagnosis/treatment facilities). In an example, the data center 910 can be a server or a group of servers and/or reside on a server or group of servers, for example. The data center 910 can also be one server or group of servers that is connected to other servers or groups of servers at separate physical locations. The data center 910 can represent single units, separate units, or groups of units in separate forms and can be implemented in hardware and/or in software. In an example, the data center 910 receives medical information from a plurality of sources. For example, the sources of clinical information can include various clinics, labs, pharmacies, as well as the patient him/herself.

The data center 910 also includes Web services 912 to provide access control and interface capability between the patient computer 920, the clinic server 930, the front desk interface 940, the physician computer 950, and the PHR database 914. Requests to store and/or retrieve data via the database 914 are routed through and approved by the data center Web services 912 according to one or more rules, preferences, and/or user profiles, for example.

In an example, the database 914 of the data center 910 represents a central database 914 for storing encrypted update-transactions for patient medical records, including usage history. In an example, the database 914 also stores the patient medical records. The data center 910 stores and controls access to encrypted information. In an example, medical records can be stored without using logic structures specific to medical records. In such a manner the database 914 is not searchable. For example, a patient's data can be encrypted with a unique patient-owned key at the source of the data. The data is then uploaded to the data center 910. The data center 910 does not process or store unencrypted data thus minimizing privacy concerns. The patient's data can be downloaded to, for example, a computer and decrypted locally with the encryption key. In an example, accessing software, for example software used by the patient and software used by the medical clinic performs the encryption/decryption.

As shown, for example, in FIG. 8, the database 914 can be structured according to clinic, patient, patient/clinic association, and document, as reflected in the database 800. Clinic information 810 can include, for example, an identifier, a name, and address, a public key, and one or more security categories. Patient information 820 can include, for example, an identifier, a password hash, and an encrypted email address. Patient/clinic association information 830 can include a clinic identifier, a patient identifier, an encrypted key, and one or more override security categories. Document information 840 can include an identifier, a patient identifier, a clinic identifier, a security category, and encrypted data, for example.

The data center 910 can maintain a registration of patients and a registration of medical clinics. Medical clinics can be registered in the data center 910 with name, address, and other identifying information. The medical clinics are issued an electronic key that is associated with a certificate. The medical clinics are also granted a security category. The security category is typically based on clinic type. In an example, the requests and data sent from medical clinics are digitally signed with the clinic's certificate and authenticated by the data center 910. Patients can be registered in the data center 910 with a patient identifier and password hash, without any identifying information. Typically, registered patients are issued a token containing a unique patient identifier and encryption key. The token can be, for example, a paper card, a magnetic card, a fob card, or some other equipment that can be used to identify the patient. A patient can access the data center 910 utilizing their token, and in an example, a user identifier and password.

As discussed above, the data center 910 is in communication, via the Web services 912, with the patient computer 920, the clinical server 930, the reception interface 940, and the physician computer 950. The data center 910, patient computer 920, clinical server 930, reception interface 940, and physician computer 950 can be in communication via any computer hardware, firmware, and/or software that can process electronic communications to/from the data center 910, patient computer 920, clinical server 930, reception interface 940, and physician computer 950.

A user can download a medical record from the data center 910, decrypt the medical record via the patient computer 920, such as a personal or handheld computer, and then process the data on a local basis, for example. For example, a viewer 922 at the patient computer 920 can be used for PHR communication, data encryption/decryption, and viewing. The viewer 922 can facilitate download of PHR data for the patient from the data center database 914 and storage of the patient data in a PHR cache 924 at the patient computer 920, for example.

Similarly, the physician computer 940 can be used to download medical record information from the data center 910. For example, medical record information can be stored in the PHR database 914 and be accessible by the physician computer 940 via the Web services 912. As another example, medical record information can be stored at the data center 910 from the clinic EMR 932 via the clinical server 930.

In certain examples, one or more of the patient computer 920, clinic server 930, front desk interface 940, and/or physician computer 950 can be used to send data to the data center 910 for medical record update. For example, a receptionist and/or patient at the front desk interface 940 can access the PHR data center 910 for PHR signup, check-in, and/or identification generation, such as via the PHR card printer 942. As another example, a user at the physician computer 950 can access the PHR data center 910 via a viewer 952 that facilitates PHR communication, encryption/description, and display of PHR data. The viewer 952 can be used to retrieve PHR data from the database 914 for storage in a PHR cache 954 of active patients for the physician, for example.

Alternatively and/or in addition, sources such as laboratory results, pharmaceutical information, patient examination information, and image acquisitions, can provide data for storage at the data center 910. In certain examples, a patient and/or authorized clinician can register or log in using a patient and/or clinician identifier, certificate, etc. Data can then be encrypted using the identifier and an encryption key and sent to the data center 910 to update a patient's medical record in the database 914. Also, the data can be normalized prior to sending to the data center 910.

In an example, data center 910, patient computer 920, clinic server 930, reception interface 940, and/or physician computer 950 can be connected to one or more of each other via network connections, for example through the Internet or private network.

Figure 10:
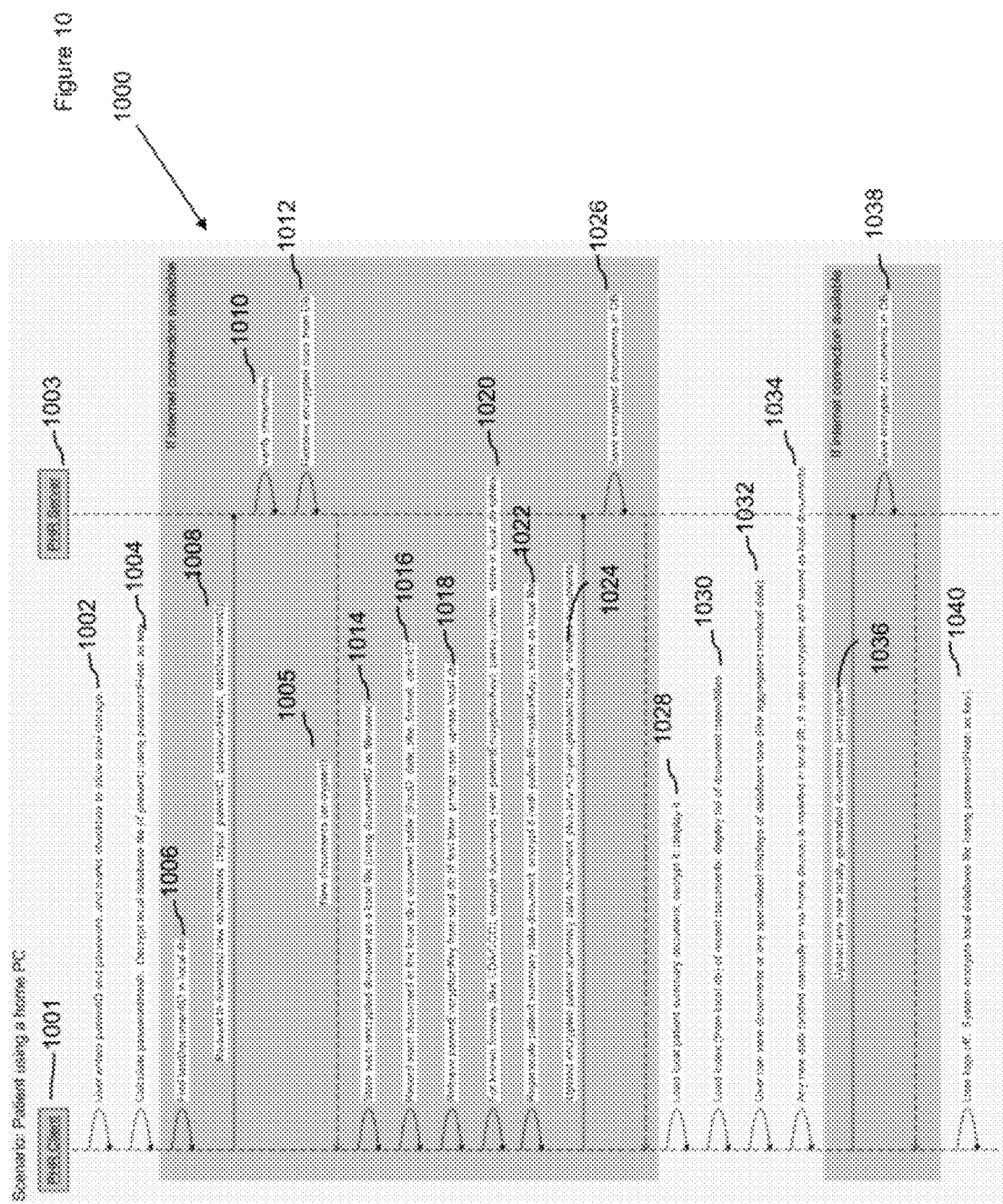
FIG. 10 illustrates an example flow diagram for a method for patient PHR access using a patient computer.

FIG. 10 illustrates an example flow diagram for a method 1000 for patient PHR access using a patient computer, such as patient computer 920, and/or other private access device. The method 1000 illustrates a series of interactions and flow of data between a PHR client 1001 and a PHR server 1003 via a patient computer, such as patient computer 920. At 1002, a user enters identification, such as a patient identifier and password, via the PHR client 1001 and selects an option to allow local storage of information. At 1004, a value, such as a password hash, is calculated. A local database file, if present, is decrypted using the password hash as the key. At 1006, a last document identifier, or alternatively, last download date, is found in the local database. At 1008, using the last document identifier or last download date, the password hash, and the patient identifier, a request to download new document(s) is sent to the PHR server 1003.

At 1010, PHR client 1001 credentials are verified (e.g., patient ID and password hash). Then, at 1012, the requested encrypted documents are retrieved from a database at or associated with the PHR server 1003. The new document(s) (encrypted) 1005 are transmitted to the PHR client 1001.

At 1014, each encrypted document is stored as a local file. For example, an encrypted PHR document can be stored locally at the PHR client 1001 using the document identifier as the file name for that document. At 1016, each document is recorded in a document table for the local database. For example, document information such as document identifier, date, title, format, clinic identifier, etc., is entered in the database document table for each document.

At 1018, a patient encryption key is retrieved from the local database. If the user is logging in for the first time on this computer, for example, the user may be prompted to enter an encryption key and update the local database. At 1020, for known document formats, such as Clinical Document Architecture (CDA), Continuity of Care Record (CCR), Continuity of Care Document format (CCD), Care Record Summary, etc., documents are decrypted with the patient encryption key. Content from the decrypted documents is parsed and stored in local database tables.

At 1022, a patient summary data document is regenerated using the newly recorded document(s). The summary document can be encrypted with the patient encryption key and stored as a local file on the PHR client 1001, for example. At 1024, the encrypted patient summary data document and any not yet uploaded locally created documents are uploaded to the PHR server 1003. At 1026, the uploaded encrypted documents are saved in a database at the PHR server 1003.

At 1028, the local patient summary document is loaded at the PHR client 1001, decrypted, and displayed. At 1030, an index of recent documents is loaded from the local database on the PHR client 1001, and a list of document information (e.g., dates, titles, etc.) can be displayed to the patient user at the patient computer 920. At 1032, the user can view document(s) and/or other displays of database data (e.g., aggregated medical data) via the PHR client 1001 at the patient computer 920 (e.g., via browser or viewer associated with the PHR client 1001 running on the patient computer 920). At 1034, new data (e.g., data added manually by the user or via home device) is inserted into the local database and is encrypted and saved as one or more local documents at the PHR client 1001.

At 1036, new locally generated encrypted document(s) are uploaded to the PHR server 1003. At 1038, the encrypted document(s) are saved in the PHR server 1003 database.

Figure 11:
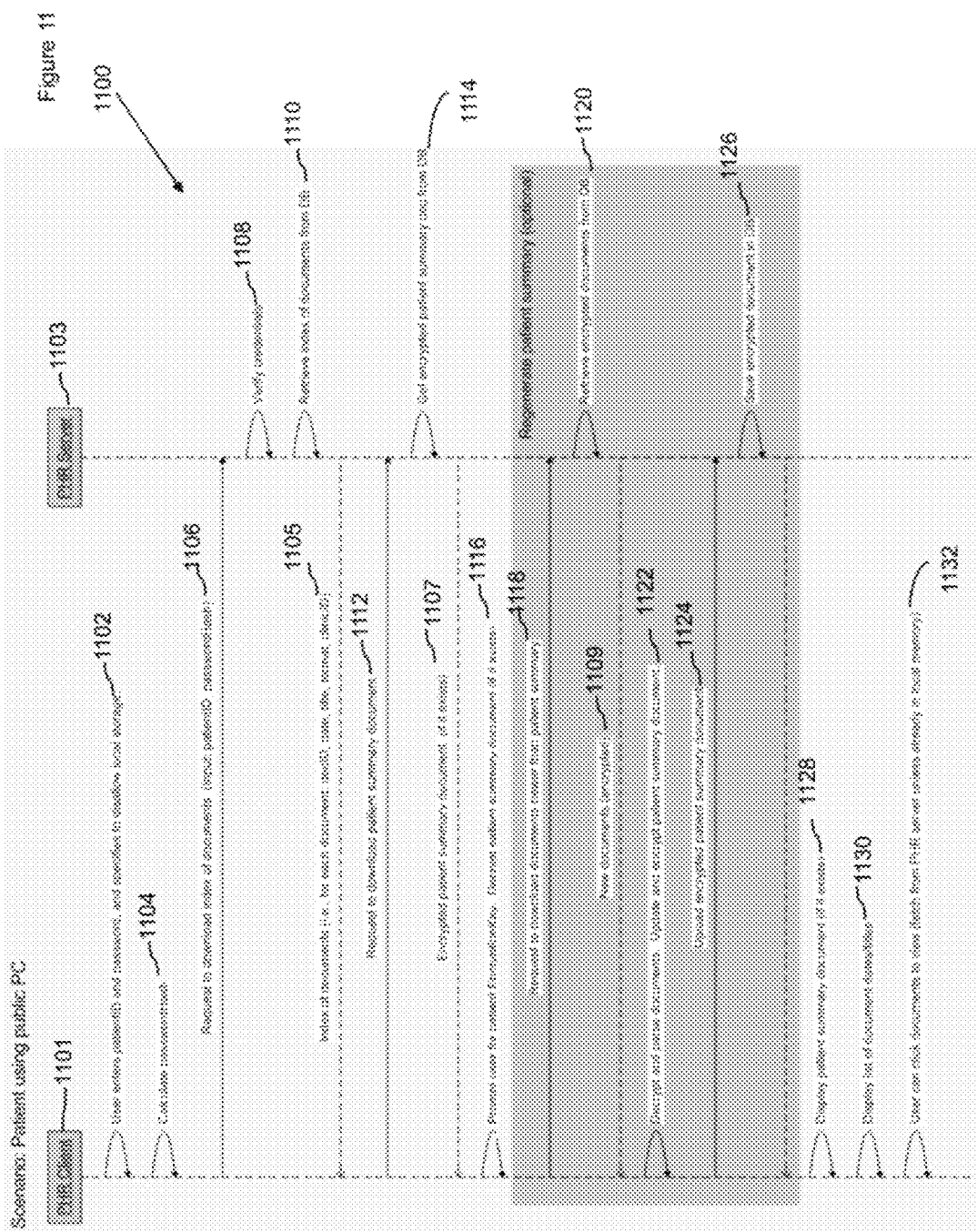
FIG. 11 illustrates an example flow diagram for a method for patient PHR access using a public computer or access device.

FIG. 11 illustrates an example flow diagram for a method 1100 for patient PHR access using a public computer or access device. The method 1100 illustrates a series of interactions and flow of data between a PHR client 1101 and a PHR server 1103 via a public computer. At 1102, a user enters identification, such as a patient identifier and password, via the PHR client 1001 and selects an option to disallow local storage of information. At 1104, a value, such as a password hash, is calculated. At 1106, using the patient identifier and password hash, a request to download an index of document(s) is sent to the PHR server 1103.

At 1108, user credentials are verified (e.g., patient ID and password hash). Then, at 1110, an index of document(s) is retrieved from a database at or associated with the PHR server 1103. The index of document(s) 1105 is transmitted to the PHR client 1101. The index can include, for example, a document identifier, date, title, format, clinic identifier, etc., for each document.

At 1112, a request to download a patient summary document is transmitted from the PHR client 1101 to the PHR server 1103. At 1114, the encrypted patient summary document is retrieved, if it exists, from the PHR sever 1103 database. The encrypted patient summary document 1107 is transmitted back to the PHR client 1101. At 1116, the user is prompted for a patient encryption key, which is used to decrypted the patient summary document.

At 1118, a request is sent from the PHR client 1101 to the PHR server 1103 to download documents newer than the patient summary. At 1120, encrypted documents newer than the patient summary are retrieved from the PHR server 1103 database. The encrypted new documents 1109 are sent to the PHR client 1101. At 1122, the encrypted new documents are decrypted and parsed. Optionally, the patient summary can be updated based on the new documents and encrypted. At 1124, the encrypted patient summary document is uploaded from the PHR client 1101 to the PHR server 1103. At 1126, the encrypted patient summary document is saved in a database at the PHR server 1103.

At 1128, the patient summary document is displayed via the PHR client 1101. At 1130, a list of document information (e.g., dates, titles, etc.) is displayed via the PHR client 1101. At 1132, the user can select (e.g., click on) one or more available documents in the list to view the document. For example, a selected document is fetched from the PHR server 1103 unless the document is already in local memory from updating the patient summary.

Figure 12:
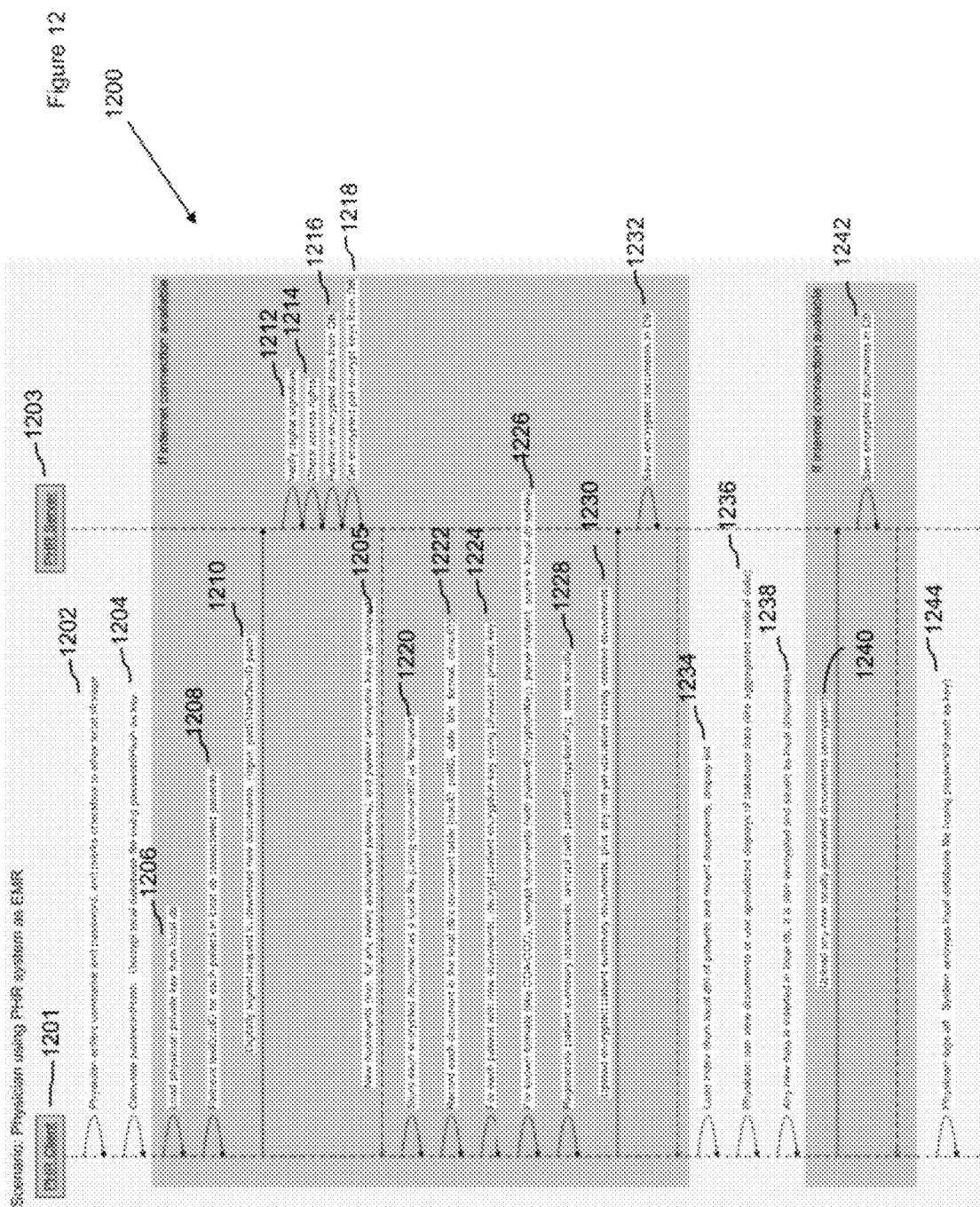
FIG. 12 illustrates an example flow diagram for a method for physician and/or other authorized clinician access to use a PHR as an electronic medical record (EMR).

FIG. 12 illustrates an example flow diagram for a method 1200 for physician and/or other authorized clinician access to use a PHR as an EMR. The method 1200 illustrates a series of interactions and flow of data between a PHR client 1201 and a PHR server 1203 via a physician or clinic computer, such as clinic server 930, reception interface 940, and/or physician computer 950, and/or other such access device. At 1202, a physician or other clinical user enters identification, such as a username and password, via the PHR client 1201 and selects an option to allow local storage of information. At 1204, a value, such as a password hash, is calculated. A local database file, if present, is decrypted using the password hash as the key.

At 1206, a physician private key is loaded from a local database. At 1208, a last document identifier is retrieved for each of the physician's patients from the local database. At 1210, a digitally signed request to download new document(s) is sent to the PHR server 1203. For example, a digitally signed request including a patient identifier and last document identifier is sent from the PHR client 1201 to the PHR server 1203.

At 1212, the digital signature is verified at the PHR server 1203. At 1214, access rights for the physician are checked. For example, the PHR server 1203 checks to determine that the physician has access rights to a particular patient's documents. Then, at 1216, encrypted documents are retrieved from a database at or associated with the PHR server 1203. At 1218, applicable encrypted patient encryption key(s) are retrieved from the PHR server 1203 database. The encrypted new document(s) 1205, including any documents for patients newly associated with the physician, are transmitted to the PHR client 1201 along with the encrypted patient encryption keys.

At 1220, each encrypted document is stored as a local file. For example, an encrypted PHR document can be stored locally at the PHR client 1201 using the document identifier as the file name for that document. At 1222, each document is recorded in a document table for the local database. For example, document information such as document identifier, patient identifier, date, title, format, clinic identifier, etc., is entered in the database document table for each document.

At 1224, for each patient with new documents, the patient encryption key is decrypted using the physician private key. At 1226, for known document formats, such as Clinical Document Architecture (CDA), Continuity of Care Record (CCR), Continuity of Care Document format (CCD), Care Record Summary, etc., documents are decrypted with the patient encryption key. Content from the decrypted documents is parsed and stored in local database tables.

At 1228, a patient summary data document is regenerated using the newly recorded document(s). The summary document can be encrypted with the patient encryption key and stored as a local file on the PHR client 1201, for example. At 1230, the encrypted patient summary data document and any not yet uploaded locally created documents are uploaded to the PHR server 1203. At 1232, the uploaded encrypted documents are saved in a database at the PHR server 1203.

At 1234, an index of patients and recent documents is loaded from the local database on the PHR client 1201 and displayed to the physician user. At 1236, the user can view document(s) and/or other displays of database data (e.g., aggregated medical data) via the PHR client 1201 (e.g., via browser or viewer associated with the PHR client 1201 running on the reception interface 940 and/or physician computer 950). At 1238, new data is inserted into the local database and is encrypted and saved as one or more local documents at the PHR client 1201.

At 1240, new locally generated encrypted document(s) are uploaded to the PHR server 1203. At 1242, the encrypted document(s) are saved in the PHR server 1203 database. At 1244, the physician logs off his or her PHR client 1201 access. The local database file is encrypted by the PHR client 1201. For example, the local database file can be encrypted using the password hash as a key.

Figure 13:
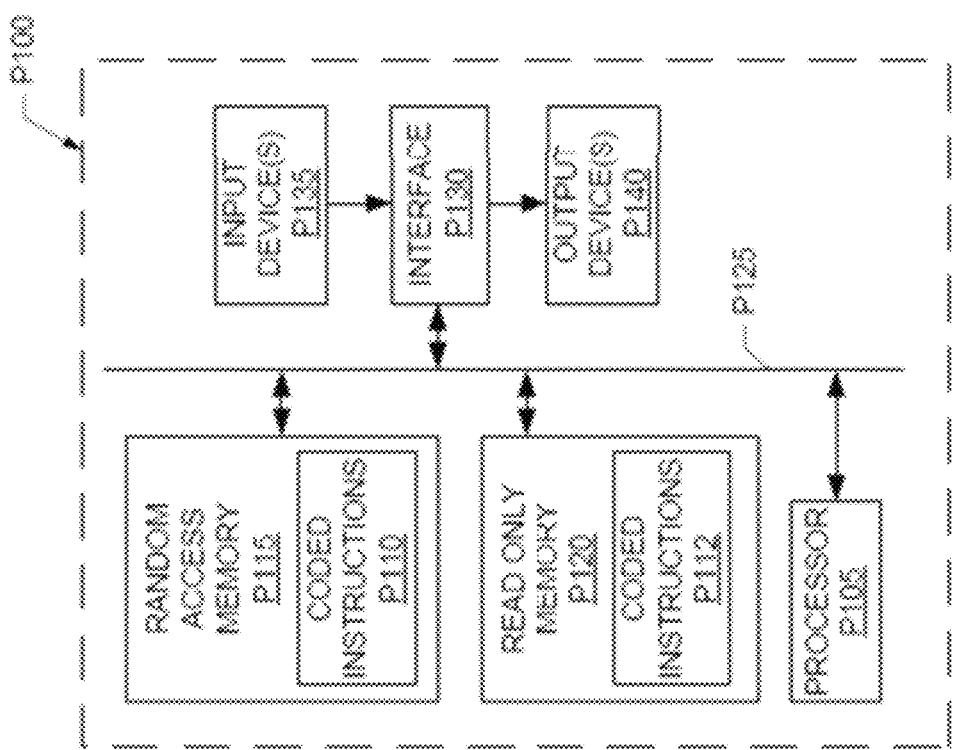
FIG. 13 is a schematic diagram of an example processor platform that may be used and/or programmed to implement the example systems and methods described herein.

FIG. 13 is a schematic diagram of an example processor platform P100 that may be used and/or programmed to implement the example systems and methods described above. For example, the processor platform P100 can be implemented by one or more general-purpose processors, processor cores, microcontrollers, etc.

The processor platform P100 of the example of FIG. 13 includes at least one general-purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example process of FIGS. 10-12 to implement the example methods and apparatus described herein.

The processor P105 is in communication with the main memory (including a ROM P120 and/or the RAM P115) via a bus P125. The RAM P115 may be implemented by dynamic random access memory (DRAM), synchronous dynamic random access memory (SDRAM), and/or any other type of RAM device, and ROM may be implemented by flash memory and/or any other desired type of memory device. Access to the memory P115 and the memory P120 may be controlled by a memory controller (not shown). The example memory P115 may be used to implement the example databases described herein.

The processor platform P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130. The input devices P135 may be used to, for example, receive patient documents from a remote PHR server and/or database. The example output devices P140 may be used to, for example, provide patient documents for review and/or storage at a remote PHR server and/or database.

Certain examples above can be applied to an architecture and components based upon Health Information Exchange (HIE) standards, such as document storage, querying, etc. Certain examples provide Web portal applications for data presentation to patients. A Web-based portal can provide an adaptive and proactive experience for users including matching technology/tools, education/information, and guided feedback based upon a patient's specific personality and lifestyle assessment, for example.

Certain embodiments provide a technical effect of local EMR/PHR functionality with secured remote storage of patient data in encrypted form. Certain embodiments provide protected access and authorized local viewing of particular patient content.

The systems and methods described above can be carried out as part of a computer readable storage medium including a set of instructions for a computer. The computer readable storage medium can include single units, separate units, can be integrated in various forms, and can be implemented in hardware and/or in software.

A technical effect of the invention is to manage consumer health in a personalized consumer healthcare context. In an example, the technical effect can be achieved by acquiring information regarding a patient in a centralized manner. A centralized system stores patient medical record data and associated audit logs in encrypted form accessible to the patient as well as authorized medical clinics. Typically, software used by the patient and software used by the medical clinic would be responsible for the encryption/decryption minimizing privacy concerns. Furthermore, the information is normalized to a standard format.

Certain examples provide a personal health record system and method of access that improves patient privacy. If patient data is handled as clear, unencrypted text at the data center at any point, the data is subject to many types of security risks. Maintaining data encryption at the data center and providing secure methods for data encryption and/or decryption on the authorized patient and/or clinical access side helps to improve security and reliability of an expansive personal health record system.

Certain examples contemplate methods, systems and computer program products on any machine-readable media to implement functionality described above. Certain examples can be implemented using an existing computer processor, or by a special purpose computer processor incorporated for this or another purpose or by a hardwired and/or firmware system, for example.

Certain examples include computer-readable media for carrying or having computer-executable instructions or data structures stored thereon. Such computer-readable media can be any available media that can be accessed by a general purpose or special purpose computer or other machine with a processor. By way of example, such computer-readable media can comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Certain examples can be practiced in a networked environment using logical connections to one or more remote computers having processors. Logical connections can include a local area network (LAN) and a wide area network (WAN) that are presented here by way of example and not limitation. Such networking environments are commonplace in office-wide or enterprise-wide computer networks, intranets and the Internet and can use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Examples of the invention can also be practiced in distributed computing environments where tasks are performed by local and remote processing devices that are linked (either by hardwired links, wireless links, or by a combination of hardwired or wireless links) through a communications network. In a distributed computing environment, program modules can be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory can include read only memory (ROM) and random access memory (RAM). The computer can also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain examples, it will be understood by those skilled in the art that various changes can be made and equivalents can be substituted without departing from the scope of the invention. In addition, many modifications can be made to adapt a particular situation or material to the teachings of the invention without departing from its scope. Therefore, it is intended that the invention not be limited to the particular embodiments and examples disclosed, but that the invention will include all embodiments and examples falling within the scope of the appended claims.

The invention claimed is:

1. A system comprising:
a local electronic medical record (EMR) system providing access to a clinician associated with a patient, the local EMR system implemented using a combination of a remote patient health record (PHR) server including a first processor configured for the remote PHR server, a local PHR client including a second processor configured for the local PHR client, and a local PHR database, each of the remote PHR server, the local PHR client, and the local PHR database unaccessible to the clinician and accessible only to the patient and authorized designees of the patient via a patient-specific encryption key, wherein the local PHR client, the remote PHR server, and the local PHR database are arranged to emulate EMR functionality and data for the local EMR system without installation and support of an onsite EMR system, wherein the remote PHR server cannot decrypt records, and wherein the local PHR client is to facilitate both secure patient access and secure clinician access to the remote PHR server for electronic patient medical information, the electronic patient medical information controlled by the patient and made accessible to the clinician via the remote PHR server and a clinician-side portal configured to enable the local EMR system for the clinician.

2. The system of claim 1, further comprising a local storage storing downloaded encrypted patient documents as separate files on a user's computer apart from the local PHR database.

3. The system of claim 1, wherein the local PHR database is rebuilt from encrypted patient documents at the remote PHR server based at least in part on at least one of a) a change at a user's computer and b) a change in the encrypted patient documents.

4. The system of claim 1, wherein patient medical data is encrypted at the PHR client and uploaded to the remote PHR server in encrypted form without saving a local copy.

5. The system of claim 1, wherein an encryption key comprises at least one of a patient encryption key and a physician private key.

6. The system of claim 1, wherein the PHR client generates a patient summary document from downloaded encrypted patient documents for display to the user via a user interface.

7. The system of claim 1, wherein the PHR client generates an index of patient documents from downloaded patient documents for display to the user via a user interface, the interface facilitating selection of a document in the index by the user for display.

8. A computer-implemented method for providing a local electronic medical record system, said method comprising:
implementing a local electronic medical record (EMR) system providing access to a clinician associated with a patient using a combination of a remote patient health record (PHR) server including a first processor configured for the remote PHR server, a local PHR client including a second processor configured for the local PHR client, and a local PHR database, each of the remote PHR server, the local PHR client, and the local PHR database unaccessible to the clinician and accessible only to the patient and authorized designees of the patient via a patient-specific encryption key, wherein implementing comprises:
arranging the local PHR client, the remote PHR server, and the local PHR database to emulate EMR functionality and data for the local EMR system without installation and support of an onsite EMR system, wherein the remote PHR server cannot decrypt records and wherein the local PHR client is to facilitate both secure patient access and secure clinician access to the remote PHR server for electronic patient medical information; and
facilitating control of the electronic patient medical information by the patient, the electronic patient medical information made accessible to the clinician via the remote PHR server and a clinician-side portal configured to enable the local EMR system for the clinician.

9. The method of claim 8, further comprising storing downloaded encrypted patient documents as separate files in local storage on a user's computer apart from the local PHR database.

10. The method of claim 8, further comprising rebuilding the local PHR database from encrypted patient documents at the remote PHR server based at least in part on at least one of a) a change at a user's computer and b) a change in the encrypted patient documents.

11. The method of claim 8, wherein the local PHR database includes encrypted patient documents for a plurality of patients associated with a clinician.

12. The method of claim 8, wherein patient medical data is encrypted at the PHR client and uploaded to the remote PHR server in encrypted form without saving a local copy.

13. The method of claim 8, further comprising generating, via the PHR client, a patient summary document from downloaded encrypted patient documents for display to the user via a user interface.

14. The method of claim 8, wherein an encryption key comprises at least one of a patient encryption key and a physician private key.

15. The method of claim 8, further comprising generating, via the PHR client, an index of patient documents from downloaded patient documents for display to the user via a user interface, the interface facilitating selection of a document in the index by the user for display.

16. A computer-readable medium including a set of instructions which, when executed on a computer, implement a local electronic medical record system comprising:
a local electronic medical record (EMR) system providing access to a clinician associated with a patient, the local EMR system implemented using a combination of a remote patient health record (PHR) server including a first processor configured for the remote PHR server, a local PHR client including a second processor configured for the local PHR client, and a local PHR database, each of the remote PHR server, the local PHR client, and the local PHR database unaccessible to the clinician and accessible only to the patient and authorized designees of the patient via a patient-specific encryption key, wherein the local PHR client, the remote PHR server, and the local PHR database are arranged to emulate EMR functionality and data for the local EMR system without installation and support of an onsite EMR system, wherein the remote PHR server cannot decrypt records, and wherein the local PHR client is to facilitate both secure patient access and secure clinician access to the remote PHR server for electronic patient medical information, the electronic patient medical information controlled by the patient and made accessible to the clinician via the remote PHR server and a clinician-side portal configured to enable the local EMR system for the clinician.

17. The computer readable medium of claim 16, further comprising storing downloaded encrypted patient documents as separate files in local storage on a user's computer apart from the local PHR database.

18. The computer readable medium of claim 16, further comprising rebuilding the local PHR database from encrypted patient documents at the remote PHR server based at least in part on at least one of a) a change at a user's computer and b) a change in the encrypted patient documents.

19. The computer readable medium of claim 16, wherein patient medical data is encrypted at the PHR client and uploaded to the remote PHR server in encrypted form without saving a local copy.

20. The computer readable medium of claim 16, further comprising generating, via the PHR client, a patient summary document from downloaded encrypted patient documents for display to the user via a user interface.

\* \* \* \* \*